United States Patent
Ouchi et al.

(10) Patent No.: US 6,508,810 B1
(45) Date of Patent: Jan. 21, 2003

(54) CONNECTING STRUCTURE FOR A FLEXIBLE TUBE AND A MOUTHPIECE OF A TREATMENT TOOL USED FOR AN ENDOSCOPE

(75) Inventors: Teruo Ouchi, Saitama (JP); Satoshi Kidooka, Tokyo (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 115 days.

(21) Appl. No.: 09/708,447

(22) Filed: Nov. 9, 2000

(30) Foreign Application Priority Data

Nov. 16, 1999 (JP) .............................. 11-324935

(51) Int. Cl.[7] .............................................. B05B 1/34
(52) U.S. Cl. ........................... 606/1; 600/157; 604/533; 604/535; 239/491
(58) Field of Search .............................. 606/1; 600/157; 604/533, 535, 164.04, 539; 239/491, 492, 493, 499, 463, 468, 475, 590, 469, 404; 169/20

(56) References Cited

U.S. PATENT DOCUMENTS

| | | | | |
|---|---|---|---|---|
| 3,844,484 A | * | 10/1974 | Masai | 239/404 |
| 4,860,731 A | * | 8/1989 | Matsuura | 600/157 |
| 5,067,655 A | * | 11/1991 | Farago et al. | 239/463 |
| 5,279,542 A | * | 1/1994 | Wilk | 600/157 |
| 5,337,730 A | * | 8/1994 | Maguire | 600/157 |
| 5,386,817 A | * | 2/1995 | Jones | 600/157 |
| 5,433,383 A | * | 7/1995 | Sundholm | 239/493 |
| 5,575,756 A | * | 11/1996 | Karasawa et al. | 600/157 |
| 5,655,608 A | * | 8/1997 | Sundholm | 169/20 |
| 6,024,301 A | * | 2/2000 | Hurley et al. | 239/492 |
| 6,086,565 A | | 7/2000 | Ouchi | |
| 6,095,970 A | | 8/2000 | Hidaka et al. | |
| 6,354,519 B1 | * | 3/2002 | Kidooka et al. | 239/491 |
| 6,409,657 B1 | * | 6/2002 | Kawano | 600/157 |

FOREIGN PATENT DOCUMENTS

JP        2517159        8/1996

* cited by examiner

Primary Examiner—Teresa Walberg
Assistant Examiner—Fadi H. Dahbour
(74) Attorney, Agent, or Firm—Greenblum & Bernstein, P.L.C.

(57) ABSTRACT

A connecting structure of a flexible tube with a mouthpiece, serving as elements of a treatment tool for an endoscope, includes at least one claw projection provided on an outer peripheral surface of a cylindrical connecting portion of the mouthpiece; and at least one claw-projection gap provided at a discontinuous portion of each claw projection. A connecting end of the flexible tube is inserted onto the cylindrical connecting portion so that at least one claw projection digs into an inner peripheral surface of the connecting end of the flexible tube. Each claw projection is provided perpendicular to the axis of the cylindrical connecting portion. A surface of each claw projection is inclined inward, toward the outer peripheral surface of the cylindrical connecting portion, in a direction so as to allow the cylindrical connecting portion to be inserted into the connecting end of the flexible tube.

11 Claims, 3 Drawing Sheets

PRIOR ART

CONNECTING STRUCTURE FOR A FLEXIBLE TUBE AND A MOUTHPIECE OF A TREATMENT TOOL USED FOR AN ENDOSCOPE

BACKGROUND OF THE INVENTION

1. Field of the Invention

The present invention relates to the structure of the connection of an end of a flexible tube, serving as an element of a treatment tool used for an endoscope, with a mouthpiece serving as an element of the same treatment tool.

2. Description of the Related Art

FIG. 1 shows the structure of the connection of one end (connecting end) of a flexible tube 90 (e.g., a flexible sheath which sheathes a flexible metal tube (not shown)) with a mouthpiece 91. The flexible tube 90 and the mouthpiece 91 are elements of a conventional treatment tool used for an endoscope. The mouthpiece 91 is provided at the rear end thereof with a cylindrical connecting portion 92 having self-locking spiral claw projections 93 formed around the cylindrical connecting portion 92. The outer edges of the self-locking spiral claw projections 93 are formed sharp in order to prevent the connecting end of the flexible tube 90 from coming off the cylindrical connecting portion 92. The connecting end of the flexible tube 90 is press-fitted snugly onto the cylindrical connecting portion 92 so as to be engaged with the spiral claw projection 93. This connecting structure is disclosed in, e.g., Japanese Utility Model No. 2,517,159.

The spiral claw projections 93 are formed as a single continuous spiral male thread-like projection. Accordingly, the flexible tube 90 cannot be fixed to the cylindrical connecting portion 92 securely even if the connecting end of the flexible tube 90 is press-fitted snugly onto the cylindrical connecting portion 92 (or even if the connecting end of the flexible tube 90 is screwed snugly on the cylindrical connecting portion 92) because the spiral claw projections 93 only slightly dig into the inner peripheral surface of the connecting end of the flexible tube 90.

For this reason, in such a conventional connecting structure, in order to firmly fix the connecting end of the flexible tube 90 with the cylindrical connecting portion 92, a cord 94 has to be wrapped around the connecting end of the flexible tube 90 tightly to reinforce the connection between the connecting end of the flexible tube 90 and the cylindrical connecting portion 92. However, there is a possibility of the cord 94 loosening when the treatment tool is in operation. If the cord 94 loosens when the treatment tool is in operation, the mouthpiece may rotate about the axis thereof relative to the flexible tube 90 and finally come off the connecting end of flexible tube 90. Furthermore, since the spiral claw projection 93 cannot deeply dig into the inner peripheral surface of the connecting end of the flexible tube 90, the outer diameter of the connecting end of the flexible tube 90 at this portion becomes undesirably larger than that of the other portion of the flexible tube 90.

SUMMARY OF THE INVENTION

It is an object of the present invention to provide a connecting structure of a flexible tube of a treatment tool used for an endoscope with a mouthpiece of the same treatment tool, wherein the flexible tube is securely connected with the mouthpiece without increasing the outer diameter of the connecting end of the flexible tube.

To achieve the object mentioned above, according to the present invention, a connecting structure for a flexible tube and a mouthpiece is provided, the flexible tube and the mouthpiece serving as elements of a treatment tool for an endoscope, the connecting structure including at least one claw projection provided on an outer peripheral surface of a cylindrical connecting portion of the mouthpiece; and at least one claw-projection gap provided on the outer peripheral surface of the cylindrical connecting portion of the mouthpiece at a discontinuous portion of each corresponding the at least one claw projection. A connecting end of the flexible tube is inserted onto the cylindrical connecting portion so that the at least one claw projection digs into an inner peripheral surface of the connecting end of the flexible tube. Each of the at least one claw projection is provided on the outer peripheral surface of the cylindrical connecting portion of the mouthpiece on a plane perpendicular to an axis of the cylindrical connecting portion. A surface of each claw projection, which is in press-contact with the inner peripheral surface of the connecting end of the flexible tube, is inclined inward, toward the outer peripheral surface of the cylindrical connecting portion, in a direction so as to allow the cylindrical connecting portion to be inserted into the connecting end of the flexible tube.

Preferably, each of the at least one claw projection is formed to have a C-shape in cross section taken along a plane normal to the axis of the cylindrical connecting portion.

Preferably, the surface of each claw projection is inclined toward the outer peripheral surface of the cylindrical connecting portion in a direction opposite to the direction of insertion of the flexible tube onto the cylindrical connecting portion.

In an embodiment, each of the flexible tube and the mouthpiece serves as an element of a spray device for an endoscope.

In an embodiment, each of the at least one claw projection includes another surface which functions to prevent the connecting end of the flexible tube from coming off the cylindrical connecting portion of the mouthpiece, and wherein an angle of the another surface relative to the outer peripheral surface of the cylindrical connecting portion is 90 degrees.

In an embodiment, each of the at least one claw projection includes another surface which functions to prevent the connecting end of the flexible tube from coming off the cylindrical connecting portion of the mouthpiece, and wherein an angle of the another surface relative to the outer peripheral surface of the cylindrical connecting portion 11a is less than 90 degrees.

According to another aspect of the present invention, a spray device used for an endoscope is provided, the spray device having a liquid-transfer tube and a spray nozzle connected to a distal end of the liquid-transfer tube, the spray nozzle including at least one spiral guide channel provided in front of the distal end of the liquid-transfer tube; a liquid whirling chamber provided in front of the at least one spiral guide channel to be connected to an outlet thereof; an orifice formed at a center of a front inner surface of the liquid whirling chamber, wherein liquid is transmitted to the liquid whirling chamber via the liquid-transfer tube and the at least one spiral guide channel spurting from the orifice in the form of a spray; at least one claw projection provided on an outer peripheral surface of a cylindrical connecting portion formed at the rear end of the spray device; and at least one claw-projection gap provided on the outer peripheral surface of the cylindrical connecting portion at a discontinuous portion of a corresponding one of the at least one claw projection. The distal end of the liquid-transfer tube is inserted onto the cylindrical connecting portion so that the at least one claw projection digs into an inner peripheral surface of the connecting end of the liquid-transfer tube. Each of the at least one claw projection is provided on the outer peripheral surface of the cylindrical connecting portion on a plane perpendicular to an axis of the cylindrical connecting portion. A surface of each claw projection, which is in press-contact with the inner peripheral surface of the connecting end of the liquid-transfer tube, is inclined inward, toward the outer peripheral surface of the cylindrical connecting portion, in a direction so as to allow the cylindrical connecting portion to be inserted into the connecting end of the liquid-transfer tube.

According to another aspect of the present invention, a mouthpiece to be inserted into an open end of a flexible tube is provided, including a cylindrical connecting portion to be contacted to an inner cylindrical surface of the open end of the flexible tube; and at least one sector claw projection provided, on a common plane perpendicular to the axis of the cylindrical connecting portion, on the outer peripheral surface of the cylindrical connecting portion so that at least one claw-projection gap is provided between the sector claw projection. A cross section, in an axial direction of the cylindrical connection portion, of the sector claw projection defines a knife edge so that the outer peripheral tip end thereof digs into the inner cylindrical surface of the flexible tube.

Preferably, the knife edge includes a leading surface that is inclined relative to normal plane to the axis of the cylindrical portion and trailing surface that is substantially normal to the axis.

The mouthpiece and the flexible tube can serve as elements of a treatment tool for an endoscope.

In an embodiment, a plurality of the at least one sector claw projection and corresponding the at least one claw-projection gap are provided at different positions with respect to the axis of the cylindrical connecting portion.

The present disclosure relates to subject matter contained in Japanese Patent Application No. 11-324935 (filed on Nov. 16, 1999) which is expressly incorporated herein by reference in its entirety.

BRIEF DESCRIPTION OF THE DRAWINGS

The invention will be discussed below in detail with reference to the drawings, in which.

DESCRIPTION OF THE PREFERRED EMBODIMENTS

Figure 2:
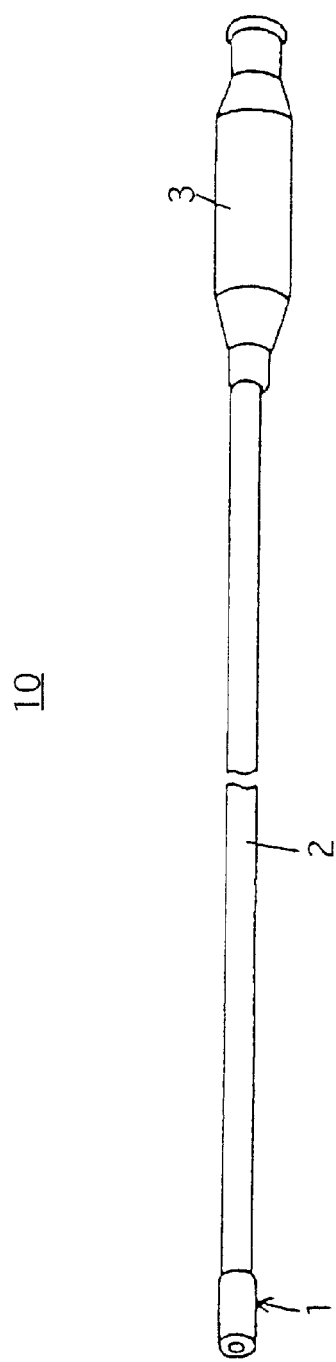
FIG. 2 is a perspective external view of an embodiment of a spray device used for an endoscope, according to the present invention.

FIG. 2 shows an embodiment of a spray device 10 for an endoscope according to the present invention. The spray device 10, which serves as a treatment tool used for an endoscope, includes a spray nozzle 1, a flexible liquid-transfer tube (flexible tube) 2, and an infusion mouthpiece 3. The liquid-transfer tube 2 can be inserted into and pulled out of a treatment tool insertion channel of an endoscope (not shown). The liquid-transfer tube 2 is made of an elastic material such as a tetrafluorinated ethylene resin. The spray nozzle 1 is fixed to the distal end of the liquid-transfer tube 2.

The infusion mouthpiece 3 is fixed to the proximal end of the liquid-transfer tube 2. A syringe tube and the like can be connected to the infusion mouthpiece 3 to infuse a liquid such as a medicinal liquid or a coloring liquid into the infusion mouthpiece 3 so as to send the liquid to the spray nozzle 1 via the liquid-transfer tube 2.

Figure 3:
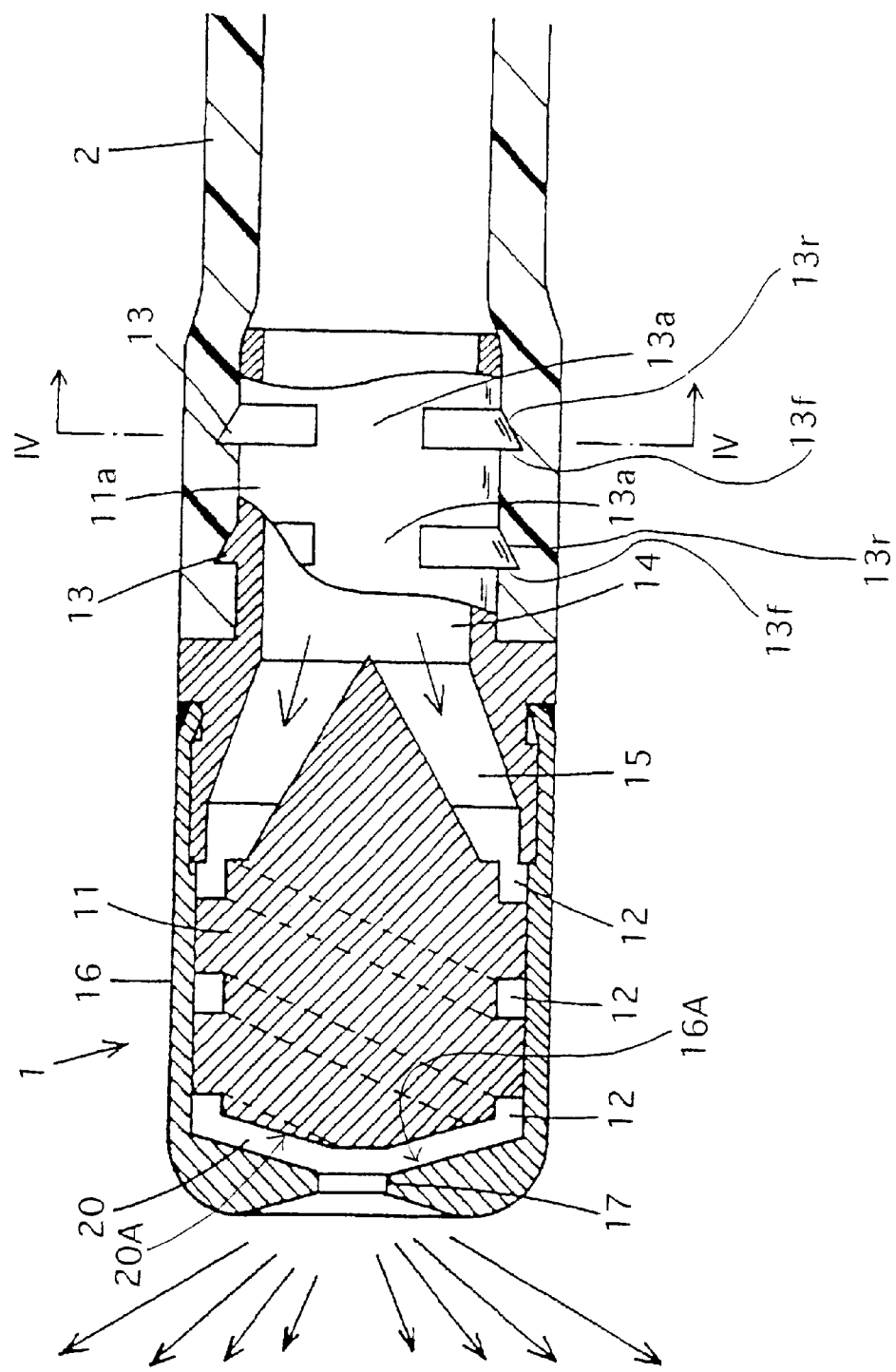
FIG. 3 is an axial cross sectional view of the distal end of the spray device shown in FIG. 2, according to the present invention, showing the connecting structure of the flexible tube with the mouthpiece.

FIG. 3 shows the internal structure of the spray nozzle 1. The spray nozzle 1 is provided with a nozzle body (mouthpiece portion) 11. The nozzle body 11 is provided on a front-half outer peripheral surface thereof with a spiral groove (spiral guide channel) 12. More than one spiral groove can be provided on the front-half outer peripheral surface of the nozzle body 11.

The nozzle body 11 is further provided at the rear end thereof with a cylindrical connecting portion (mouthpiece portion) 11a to which the distal end of the liquid-transfer tube 2 is fixed. A channel 14 which is formed in the cylindrical connecting portion 11a along the axis thereof is connected with the spiral groove 12 via connecting channels 15 formed in the middle of the nozzle body 11.

The spray nozzle 1 is further provided with an end cap 16. The end cap 16 is provided at the front end thereof with an orifice 17 and is snugly fitted on substantially a front half of the nozzle body 11 in a manner so as to close the entire peripheral opening of the spiral groove 12. Due to this structure, the spiral groove 12 functions as a liquid guide channel through which liquid runs from the liquid-transfer tube 2 to the orifice 17.

The spray nozzle 1 is provided, in the end cap 16 between an inner end surface 16A of the end cap 16 and a front end surface (left end surface as viewed in FIG. 3) of the nozzle body 11, with a liquid whirling chamber 20. The inlet and outlet of the spiral groove (spiral channel) 12 are connected with the connecting channels 15 and the liquid whirling chamber 20, respectively. The liquid whirling chamber 20 is shaped so that the liquid, which spurts from the outlet of the spiral groove 12, whirls about the axis of the spray nozzle 1 (i.e., the axis of the liquid-transfer tube 2) in the liquid whirling chamber 20. The axial center of the orifice 17 is substantially coincident with that of the liquid whirling chamber 20.

The front end surface 20A of the nozzle body 11, which defines the rear inner surface of the liquid whirling chamber 20, is formed as a substantially convex circular conical surface. On the other hand, the inner end surface 16A of the end cap 16, which defines the front inner surface of the liquid whirling chamber 20, is also formed as a substantially circular conical surface which has a concave shape corresponding to the front end surface 20A of the nozzle body 11.

Therefore, the front end surface 20A of the nozzle body 11 and the inner end surface 16A of the end cap 16 are substantially parallel to each other. Due to such structure of the spray device 1, liquid (e.g., a medicinal liquid or a coloring liquid) which is transmitted via the liquid-transfer tube 2 from the proximal end thereof spurts from the orifice 17 as spray via the spiral groove 12 and the liquid whirling chamber 20 while whirling in the liquid whirling chamber 20.

The cylindrical connecting portion 11a of the nozzle body 11 is provided on an outer peripheral surface thereof with two self-locking claw projections 13 which are spaced apart from each other in the direction of the axis of the cylindrical connecting portion 11a.

Although the two claw projections 13 are formed on the outer peripheral surface of the cylindrical connecting portion 11a of the nozzle body 11 to be spaced apart from each other in the direction of the axis of the cylindrical connecting portion 11a, the number of the claw projections 13 is not limited solely to two, but can be one or more than two.

Figure 4:
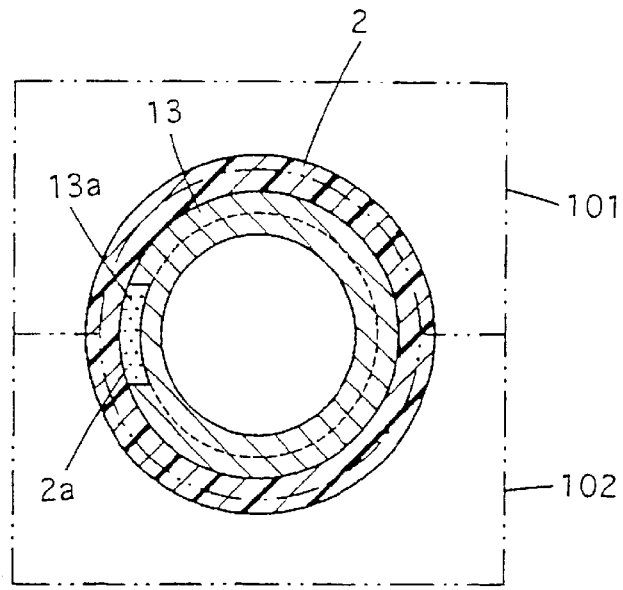
FIG. 4 is a cross sectional view of the distal end of the spray device shown in FIG. 2, taken along IV—IV line shown in FIG. 3, looking in the direction of the appended arrows.

Each of the two claw projections 13 is formed circumferentially on the outer peripheral surface of the cylindrical connecting portion 11a of the nozzle body 11 in a plane perpendicular to the axis of the cylindrical connecting portion 11a to have a C-shape in cross section taken along a plane normal to the axis thereof (see FIG. 4). Front face 13f of each claw projection 13 extends normal to the outer peripheral surface of the cylindrical connecting portion 11a of the nozzle body 11, while rear inclined face (leading surface) 13r of each claw projection 13, which is in press-contact with the inner peripheral surface of the connecting end of the liquid-transfer tube 2, is inclined toward the outer peripheral surface of the cylindrical connecting portion 11a of the nozzle body 11 by a predetermined angle in the range of, e.g., approximately 20 to 60 degrees. The edge of each claw projection 13 that is formed between the front face (trailing surface) 13f and the rear inclined face 13r is razor sharp. The front face 13f of each claw projection 13 functions so as to prevent the connecting end of the liquid-transfer tube 2 from coming off said cylindrical connecting portion 11a.

Each of the two claw projections 13 is formed as a C-shape in cross section as mentioned above, so that each claw-projection gap 13a is defined by the nozzle body 11 and at the discontinuous portion of the corresponding claw projection 13. In the illustrated embodiment shown in FIG. 3, although the two claw-projection gaps 13a are provided on the cylindrical connecting portion 11a of the nozzle body 11 at the same circumferential position about the axis of the spray nozzle 1, the two claw-projection gaps 13a can be provided at different circumferential positions about the axis of the spray nozzle 1. Furthermore, more than one claw-projection gap can be provided on the outer peripheral surface of the cylindrical connecting portion 11a of the nozzle body 11 at each discontinuous portion of the claw projection 13.

The cylindrical connecting portion 1a of the nozzle body 11 is press-fitted in the connecting end of the liquid-transfer tube 2. The inner diameter of the liquid-transfer tube 2 is smaller than the outer diameter of the cylindrical connecting portion 11a, so that the connecting end of the liquid-transfer tube 2 is fitted on the cylindrical connecting portion 11a with the diameter of the connecting end of the liquid-transfer tube 2 being expanded. An operation of inserting the cylindrical connecting portion 11a of the nozzle body 11 into the connecting end of the liquid-transfer tube 2 can be carried out easily because the rear inclined face 13r of each claw projection 13, which is in press-contact with the inner peripheral surface of the connecting end of the liquid-transfer tube 2, is inclined towards the outer peripheral surface of the cylindrical connecting portion 11a of the nozzle body 11 in a direction opposite to the direction of inserting the liquid-transfer tube 2 onto the cylindrical connection portion 11a; i.e., the rear inclined face 13r is inclined inwards in a rearward direction. Accordingly, the connecting end of the liquid-transfer tube 2 can be easily inserted onto cylindrical connecting portion 11a.

Once the cylindrical connecting portion 11a of the nozzle body 11 has been fitted securely into the connecting end of the liquid-transfer tube 2, the nozzle body 11 and the liquid-transfer tube 2 are forcibly turned relative to each other about the axis of the spray nozzle 1 by at least a predetermined number of turns. This causes the sharp edge of each claw projection 13 to scrape off a corresponding contacting surface on the inner peripheral surface of the connecting end of the liquid-transfer tube 2. As a result, swarf (chippings) 2a from the liquid-transfer tube 2, which is produced by scraping each claw projection 13 against the inner surface of the liquid-transfer tube 2, gathers in each claw-projection gap 13a.

Accordingly, there is room for the swarf (chippings) 2a of the liquid-transfer tube 2 to gather in the spray nozzle 1 because of the claw-projection gap 13a which is provided at the discontinuous portion of each claw projection 13 on the outer peripheral surface of the cylindrical connecting portion 11a of the nozzle body 11. Therefore, if the nozzle body 11 and the liquid-transfer tube 2 are forcibly turned relative to each other about the axis of the spray nozzle 1 by at least a predetermined number of turns, the sharp edge of each claw projection 13 deeply scrapes off a corresponding contacting surface on the inner peripheral surface of the connecting end of the liquid-transfer tube 2, so that each claw projection 13 deeply digs into the inner peripheral surface of the connecting end of the liquid-transfer tube 2.

In order to make each claw projection 13 deeply dig into the inner peripheral surface of the connecting end of the liquid-transfer tube 2, a pair of pressing members (shown by two-dot chain lines in FIG. 4) 101 and 102 which together form an inner cylindrical wall whose diameter is slightly smaller than the outer diameter of the liquid-transfer tube 2 is preferably used. The nozzle body 11 and the liquid-transfer tube 2 only need to be forcibly turned relative to each other about the axis of the spray nozzle 1 by at least a predetermined number of turns while the connecting end of the liquid-transfer tube 2 is tightly held by the pair of pressing members 101 and 102 from the outside of the connecting end of the liquid-transfer tube 2.

Figure 1:
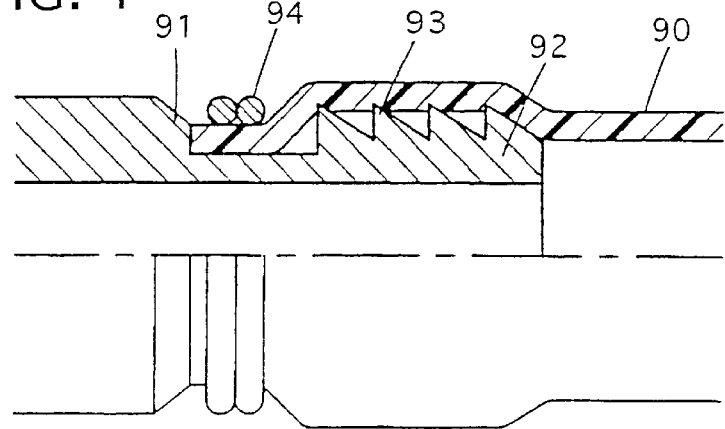
FIG. 1 is an axial cross sectional view of the connecting end of a flexible tube serving as an element of a conventional treatment tool used for an endoscope and a mouthpiece serving as an element of the same treatment tool, showing the conventional connecting structure of the flexible tube with the mouthpiece.

Due to the structure of the connection of the connecting end of the liquid-transfer tube 2 with the cylindrical connecting portion 11a of the nozzle body 11, a cord such as the cord 94 shown in FIG. 1 does not have to be wrapped around the connecting end of the liquid-transfer tube 2 to reinforce the connection between the connecting end of the liquid-transfer tube 2 and the cylindrical connecting portion 11a since the connecting end of the liquid-transfer tube 2 is securely connected with the cylindrical connecting portion 11a. The cylindrical connecting portion 11a of the nozzle body 11 does not come off the connecting end of the liquid-transfer tube 2 even if the cylindrical connecting portion 11a and the liquid-transfer tube 2 are turned relative to each other about the axis of the spray nozzle 1. Furthermore, unlike the conventional case shown in FIG. 1, the diameter of the connecting end of the liquid-transfer tube 2 either does not increase, or increases by a minimal amount.

Figure 5:
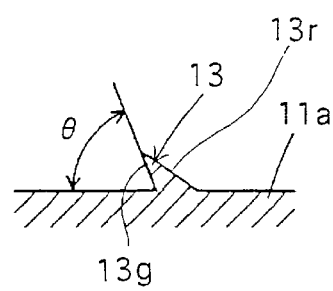
FIG. 5 is a cross sectional view of another embodiment of a self-locking claw projection that is provided around the mouthpiece of the spray device shown in FIG. 2.

The present invention is not limited solely to the above-illustrated particular embodiment. For instance, the shape of each claw projection 13 can be modified in a manner as shown in FIG. 5. As shown in FIG. 5, the angle θ of the front face 13g of each claw projection 13 relative to the outer peripheral surface of the cylindrical connecting portion 11a of the nozzle body 11 can be set at less than 90 degrees (θ<90°).

Although the present invention is applied to the structure of the connection of a flexible tube of a spray device with a mouthpiece of the same, the present invention can be applied to a structure of a similar connection of any other treatment tool.

As can be understood from the foregoing, according to the connecting structure to which the present invention is applied, since at least one claw-projection gap is provided on the outer peripheral surface of the cylindrical connecting portion of said mouthpiece at a discontinuous portion of each corresponding claw projection, there is room for the swarf (chippings) of the flexible tube, which are produced by a scraping of each claw projection, to gather in the treatment tool. Accordingly, the sharp edge of each claw projection can deeply scrape off a corresponding contacting surface on the inner peripheral surface of the connecting end of the flexible tube, so that each claw projection can deeply dig into the inner peripheral surface of the connecting end of the flexible tube. Consequently, the connecting end of the flexible tube can be securely connected with the mouthpiece without increasing the diameter of the connecting end of the flexible tube.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A connecting structure for a flexible tube and a mouthpiece, said flexible tube and said mouthpiece serving as elements of a treatment tool for an endoscope, said connecting structure comprising:

at least one claw projection provided on an outer peripheral surface of a cylindrical connecting portion of said mouthpiece; and at least one claw-projection gap provided on said outer peripheral surface of said cylindrical connecting portion of said mouthpiece at a discontinuous portion of each corresponding said at least one claw projection;

wherein a connecting end of said flexible tube is inserted onto said cylindrical connecting portion so that said at least one claw projection digs into an inner peripheral surface of said connecting end of said flexible tube;

wherein each of said at least one claw projection is provided on said outer peripheral surface of said cylindrical connecting portion of said mouthpiece on a plane perpendicular to an axis of said cylindrical connecting portion; and wherein a surface of each claw projection, which is in press-contact with said inner peripheral surface of said connecting end of said flexible tube, is inclined inward, toward said outer peripheral surface of said cylindrical connecting portion, in a direction so as to allow said cylindrical connecting portion to be inserted into said connecting end of said flexible tube.

2. The connecting structure according to claim 1, wherein each of said at least one claw projection is formed to have a C-shape in cross section taken along a plane normal to said axis of said cylindrical connecting portion.

3. The connecting structure according to claim 1, wherein said surface of each claw projection is inclined toward said outer peripheral surface of said cylindrical connecting portion in a direction opposite to the direction of insertion of said flexible tube onto said cylindrical connecting portion.

4. The connecting structure according to claim 1, wherein each of said flexible tube and said mouthpiece serves as an element of a spray device for an endoscope.

5. The connecting structure according to claim 1, wherein each of said at least one claw projection comprises another surface which functions to prevent said connecting end of said flexible tube from coming off said cylindrical connecting portion of said mouthpiece, and wherein an angle of said another surface relative to said outer peripheral surface of said cylindrical connecting portion is 90 degrees.

6. The connecting structure according to claim 1, wherein each of said at least one claw projection comprises another surface which functions to prevent said connecting end of said flexible tube from coming off said cylindrical connecting portion of said mouthpiece, and wherein an angle of said another surface relative to said outer peripheral surface of said cylindrical connecting portion is less than 90 degrees.

7. A spray device used for an endoscope, said spray device having a liquid-transfer tube and a spray nozzle connected to a distal end of said liquid-transfer tube, said spray nozzle comprising:

at least one spiral guide channel provided in front of said distal end of said liquid-transfer tube;

a liquid whirling chamber provided in front of said at least one spiral guide channel to be connected to an outlet thereof;

an orifice formed at a center of a front inner surface of said liquid whirling chamber, wherein liquid is transmitted to said liquid whirling chamber via said liquid-transfer tube and said at least one spiral guide channel spurting from said orifice in the form of a spray;

at least one claw projection provided on an outer peripheral surface of a cylindrical connecting portion formed at the rear end of said spray device; and at least one claw-projection gap provided on said outer peripheral surface of said cylindrical connecting portion at a discontinuous portion of a corresponding one of said at least one claw projection;

wherein said distal end of said liquid-transfer tube is inserted onto said cylindrical connecting portion so that said at least one claw projection digs into an inner peripheral surface of said connecting end of said liquid-transfer tube;

wherein each of said at least one claw projection is provided on said outer peripheral surface of said cylindrical connecting portion on a plane perpendicular to an axis of said cylindrical connecting portion; and wherein a surface of each claw projection, which is in press-contact with said inner peripheral surface of said connecting end of said liquid-transfer tube, is inclined inward, toward said outer peripheral surface of said cylindrical connecting portion, in a direction so as to allow said cylindrical connecting portion to be inserted into said connecting end of said liquid-transfer tube.

8. A mouthpiece to be inserted into an open end of a flexible tube, comprising:

a cylindrical connecting portion to be contacted to an inner cylindrical surface of said open end of the flexible tube; and at least one sector claw projection provided, on a common plane perpendicular to the axis of the cylindrical connecting portion, on said outer peripheral surface of said cylindrical connecting portion so that at least one claw-projection gap is provided between said sector claw projection;

wherein a cross section, in an axial direction of said cylindrical connection portion, of said sector claw projection defines a knife edge so that the outer peripheral tip end thereof digs into the inner cylindrical surface of the flexible tube.

9. The mouthpiece according to claim 8, wherein said knife edge comprises a leading surface that is inclined relative to normal plane to the axis of the cylindrical portion and trailing surface that is substantially normal to the axis.

10. The mouthpiece according to claim 8, wherein said mouthpiece and said flexible tube serve as elements of a treatment tool for an endoscope.

11. The mouthpiece according to claim 8, wherein a plurality of said at least one sector claw projection and corresponding said at least one claw-projection gap are provided at different positions with respect to the axis of said cylindrical connecting portion.

* * * * *